(12) United States Patent
Bruce et al.

(10) Patent No.: US 7,799,810 B2
(45) Date of Patent: Sep. 21, 2010

(54) ORGANIC COMPOUNDS

(75) Inventors: Ian Bruce, Horsham (GB); Gabriele Weitz Schmidt, Bad Krozingen (DE)

(73) Assignee: Novartis AG, Basel (CH)

( * ) Notice: Subject to any disclaimer, the term of this patent is extended or adjusted under 35 U.S.C. 154(b) by 77 days.

(21) Appl. No.: 12/308,338

(22) PCT Filed: Jun. 25, 2007

(86) PCT No.: PCT/EP2007/005599

§ 371 (c)(1),
(2), (4) Date: Dec. 11, 2008

(87) PCT Pub. No.: WO2008/000421

PCT Pub. Date: Jan. 3, 2008

(65) Prior Publication Data

US 2010/0120865 A1 May 13, 2010

(30) Foreign Application Priority Data

Jun. 26, 2006 (GB) .................................. 0612630.4

(51) Int. Cl.
*A01N 43/40* (2006.01)
*A61K 31/44* (2006.01)
(52) U.S. Cl. ...................................... 514/341; 548/161
(58) Field of Classification Search ........................ None
See application file for complete search history.

(56) References Cited

FOREIGN PATENT DOCUMENTS

| WO | WO 2004/096797 | 11/2004 |
|---|---|---|
| WO | WO 2005/021519 | 3/2005 |
| WO | WO 2005021519 A2 * | 3/2005 |
| WO | WO 2006/046035 | 5/2006 |

OTHER PUBLICATIONS

International Search Report, PCT/EP2007/005599, Mar. 31, 2008.

* cited by examiner

*Primary Examiner*—Brandon J Fetterolf
*Assistant Examiner*—Jean Cornet
(74) *Attorney, Agent, or Firm*—Paul D. Strain, Esq.; Fanelli Strain & Haag PLLC

(57) ABSTRACT

The present invention concerns a compound of formula (I), or a pharmaceutically acceptable salt, or solvate thereof, wherein the groups Ri- Rs are defined in the description, to compositions and use of the compounds in the treatment of diseases ameloriated by inhibition of phosphatidylinositol 3-kinase.

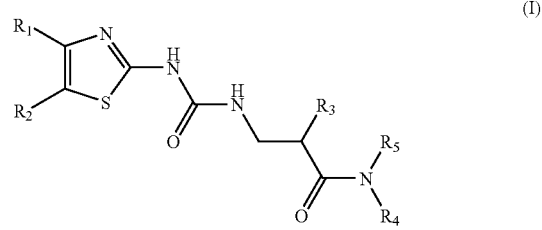

(I)

7 Claims, No Drawings

ORGANIC COMPOUNDS

The present invention relates to isoxazol-3-yl-urea derivatives, process for their production, their uses and pharmaceutical compositions containing them.

More particularly, the invention provides a compound of formula I

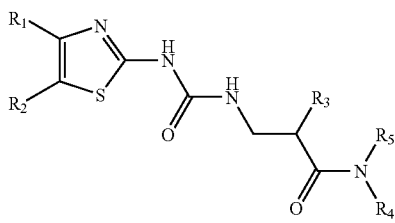

wherein
- $R_1$ is $C_{1-3}$alkyl;
- $R_2$ is phenyl, naphthyl or biphenylyl, each being optionally substituted by one or more substituents selected from halogen, $SO_2C_{1-3}$alkyl, acyl and a 5 or 6 membered heteroaryl; or an optionally substituted 5- or 6-membered heteroaryl;
- $R_3$ is H or $C_{1-3}$alkyl;
- $R_4$ is phenyl, naphthyl or biphenylyl, each being optionally substituted by $C_{1-4}$alkyl; or an optionally substituted 5- or 6-membered heteroaryl comprising at least one N as heteroatom; provided that $R_4$ is other than naphthyl when $R_2$ is phenyl substituted by $SO_2C_{1-3}$alkyl and optionally halogen; and
- $R_5$ is H or $C_{1-4}$alkyl;

or a salt thereof.

Acyl may be a radical $R_aCO$ wherein $R_a$ is $C_{1-4}$-alkyl, $C_{3-6}$cycloalkyl, phenyl or benzyl.

5- or 6-Membered heteroaryl may comprise a second heteroatom selected from N, O and S. Examples of 5 or 6 membered heteroaryl include e.g. pyrrazolyl, imidazolyl, pyrrolyl; isoxazolyl, pyridyl or thienyl. Heteroaryl may be mono- or di-substituted by $C_{1-4}$alkyl, e.g. $CH_3$. The substituent may be attached either to a carbon and/or nitrogen atom. The heteroaryl suitably comprises at least one nitrogen atom and/or a sulphur atom within the ring. In certain embodiments, the heteroaryl group comprises at least one nitrogen atom within the ring.

Preferably naphthyl as $R_4$ is unsubstituted.

Halogen may be fluorine, chlorine or bromine, preferably fluorine or chlorine.

The following significances are preferred independently, collectively or in any combination or sub-combination:
1. $R_1$ is $CH_3$
2. $R_2$ is substituted phenyl, e.g. as disclosed in the examples.
3. $R_2$ is phenyl monosubstituted by heteroaryl, e.g. pyrrazolyl.
4. $R_2$ is unsubstituted 5 or 6 membered heteroaryl, e.g. pyridyl.
5. $R_3$ is H.
6. $R_4$ is unsubstituted naphthyl
7. $R_4$ is unsubstituted or substituted heteroaryl; e.g. as disclosed in the examples.
8. $R_5$ is H.

The compounds of formula I may exist in free form or in salt form, e.g. addition salts with e.g. organic or inorganic acids, for example, hydrochloric acid or acetic acid.

When the compounds of formula I have asymmetric centers in the molecule, various optical isomers are obtained. The present invention also encompasses enantiomers, racemates, diastereoisomers and mixtures thereof. For example, the carbon atom bearing an alkyl group as $R_3$ may have the R or S configuration.

The present invention also includes a process for the production of a compound of formula I, which process comprises reacting a compound of formula II

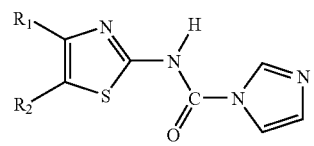

wherein $R_1$ and $R_2$ are as defined above, with a compound of formula III

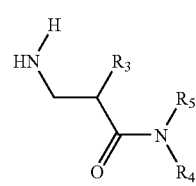

wherein $R_3$, $R_4$ and $R_5$ are as defined above, and recovering the resulting compound of formula I in free form or in form of a salt, and, where required converting the compound of formula I obtained in free form into the desired salt form or vice versa.

The process may be performed according to methods known in the art, or as disclosed below in the Examples. For example a compound of formula II may be reacted with a compound of formula III in a solvent, e.g. dimethylformamide, in the presence of a base e.g. an organic amine, e.g. triethylamine.

Compounds of formula II, used as starting materials may be prepared by reacting a compound of formula IV

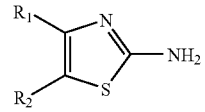

wherein $R_1$ and $R_2$ are as defined above, with carbonyldiimidazole. The reaction may be performed in a suitable solvent, e.g. as disclosed in WO05/021519A2 or WO04/096797A1, or as described thereafter.

Compounds of formula IV may be prepared e.g. by a method as disclosed in WO05/021519A2 or WO04/096797A1. Compounds of formula IV may also be prepared by reacting a compound of formula V $$R_2\text{-Hal} \qquad \qquad V$$

wherein $R_2$ is as defined above and Hal is Cl, Br or I,
with a compound of formula VI

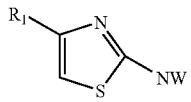
VI wherein $R_1$ is as defined above and W is a nitrogen protecting group, e.g. acetyl.

The reaction may be carried out with a catalyst, e.g. a palladium catalyst, such as Pd(t-butyl)$_3$, in the presence of a base, e.g. caesium carbonate, in a suitable solvent, e.g. dimethylformamide, at elevated temperatures. The reaction may be followed by removal of the protecting group W under standard conditions.

Alternatively compounds of formula IV may be prepared by reaction of a compound of formula VII

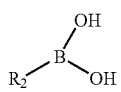
VII wherein $R_2$ is as defined above,
with a compound of formula VIII

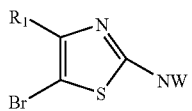
VIII wherein $R_1$ and W are as defined above. W may also be benzhydrylidene.

The reaction may be carried out with a catalyst, e.g. a palladium catalyst, such as tetrakis triphenyl phosphine palladium (0), in the presence of a base, e.g. caesium carbonate, in a suitable solvent, e.g. dioxane/water, at elevated temperature, followed by removal of the protecting group W, under standard conditions.

Compounds of formulae V and VII are commercially available or may be prepared in accordance with known methods.

Compounds of formula III may be prepared by coupling a compound of formula IX

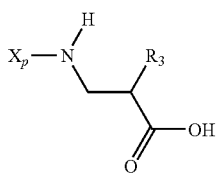
IX wherein $R_3$ is as defined above and $X_p$ is an amino protecting group, e.g. as used in a coupling reaction,
with a compound of formula X

X wherein $R_4$ and $R_5$ are as defined above, followed by deprotection of the amino protecting group. The amino protecting group X may preferably be a t-butyloxycarbonyl (BOC) or benzyloxycarbonyl (CbZ) group and the preferred method of deprotection is treatment with TMS iodide as described by Lott, Richard S.; Chauhan, Virander S.; Stammer, Charles H. Trimethylsilyl iodide as a peptide deblocking agent; Journal of the Chemical Society, Chemical Communications (1979), (11), 495-6.

Compounds of formulae IX and X are commercially available.

Insofar as the production of the starting materials is not particularly described, the compounds are either known or may be prepared analogously to methods known in the art, e.g. in WO 05/021519 or WO04/096797, or as disclosed hereinafter.

The following Examples are illustrative of the invention, without any limitation. Abbreviations used are as follows: CDI is 1,1'-carbonyldiimidazole, DCM is dichloromethane, DMF is dimethylformamide, DMSO is dimethylsulfoxide, TEA is triethylamine, THF is tetrahydrofuran, EtOAc is ethyl acetate, EtOH is ethanol, IPA is iso-propylalcohol, MeOH is methanol, MeCN is acetonitrile, TLC is thin-layer chromatography, WSCD is water soluble carbodiimide, HOAT is 1-hydroxy-7-azabenzo-triazole, TMSI is trimethyliodosilane, Pd$_2$(dba)$_3$ is tris(dibenzylideneacetone) palladium (0), PCy$_3$ is tricyclohexyl phosphine.

Intermediate A1: Imidazole-1-carboxylic acid [5-(4-acetyl-phenyl)-4-methyl-thiazol-2-yl]-amide Step 1:
Benzhydrylidene-(4-methyl-thiazol-2-yl)-amine

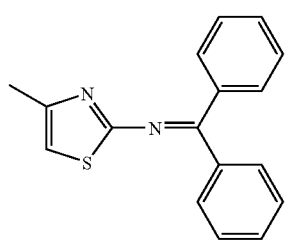

Benzophenone imine (39.8 g, 0.22 mol) is added to a solution of 2-amino-4-methyl-1,3-thiazole (30 g, 260 ml) in toluene (450 ml) and heated at reflux under an inert atmosphere for 18 h. The mixture is cooled to room temperature and washed with citrate buffer (2×250 ml), water (2×250 ml), brine (2×250 ml), dried (MgSO$_4$ and decolourising charcoal), filtered and evaporated to an orange solid.

Step 2: Benzhydrylidene-(5-bromo-4-methyl-thaizol-2-yl)-amine

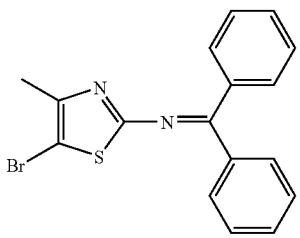

N-Bromosuccimide (26.8 g, 0.15 mol) is added to a solution of benzhydrylidene-(4-methyl-thiazol-2-yl)-amine (41.9 g, 0.15 mol) in glacial acetic acid (200 ml) and stirred for 1.25 h. The solid is filtered off and dried in vacuo. This is dissolved in DCM (400 ml) and washed with sodium bicarbonate solution (2×400 ml), water (2×400 ml), brine (2×400 ml), dried (MgSO$_4$), filtered and evaporated to yield a yellow solid which is dried in vacuo.

Step 3: 1-{4-[2-(Benzhydrylidene-amino)-4-methyl-thiazol-5-yl]-phenyl}-ethanone

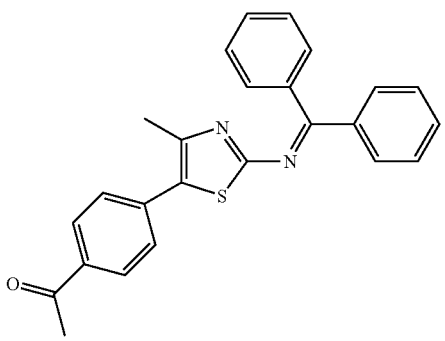

4-Acetylphenyl boronic acid (1.8 g, 0.011 mol, 1.1 eq), tetrakistriphenylphosphine palladium(0) (0.7 g, 0.6 mmol), caesium carbonate (9.8 g, 0.03 mol) in water (10 ml), are added to a solution of benzhydrylidene-(5-bromo-4-methyl-thiazol-2-yl)-amine (3.5 g, 0.01 mol) in dioxane (80 ml) and heated at reflux for 6 h. The solvent is removed in vacuo, to yield an oily suspension which is partitioned between DCM (75 ml) and sat. sodium bicarbonate (75 ml). The layers are separated and the organics washed with water (75 ml) and brine (75 ml), dried (MgSO$_4$ and charcoal), filtered and evaporated to a brown solid.

Step 4: 1-[4-(2-Amino-4-methyl-thiazol-5-yl)-phenyl]-ethanone

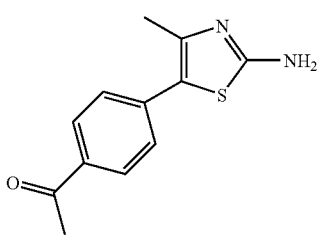

2M hydrochloric acid (45 ml) is added to 1-{4-[benzhydrylidene-amino]-4-methyl-thiazol-5-yl}-phenyl}-ethanone (4.0 g, 0.01 mol) in THF (175 ml) and stirred for 1 h. The mixture is partitioned between 0.5 M hydrochloric acid (50 ml), iso-hexane (100 ml) and EtOAc (50 ml). The aqueous phase is basified with 4M NaOH (30 ml) and extracted with DCM (2×100 ml). The organics are dried (MgSO$_4$), filtered and evaporated to a yellow solid.

Step 5: Imidazole-1-carboxylic acid [5-(4-acetyl-phenyl)-4-methyl-thiazol-2-yl]-amide

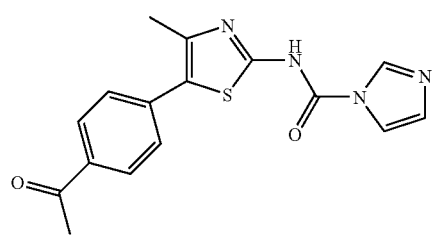

A solution of 1-[4-(2-amino-4-methyl-thiazol-5-yl)-phenyl]-ethanone (0.57 g, 2.45 mmol) is dissolved in a mixture of THF (10 ml) and DCM (20 ml) and heated in an oil bath set to 50° C. CDI is added (0.64 g, 3.92 mmol) and the reaction mixture heated at 50° C. for a further 2 hours in which a pale yellow precipitate forms. After cooling to room temperature the precipitate is filtered, washed with DCM and dried under high vacuum to yield the title compound.

Intermediate A2: Imidazole-1-carboxylic acid [4-methyl-5-(4-pyrazol-1-yl-phenyl)-thiazol-2-yl]-amide

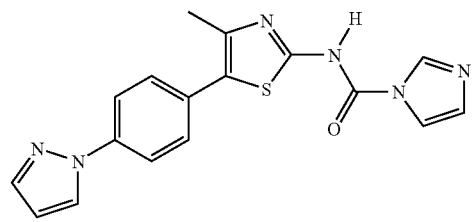

Step 1: 1-[4-(2-Nitro-propyl)-phenyl]-1H-pyrazole

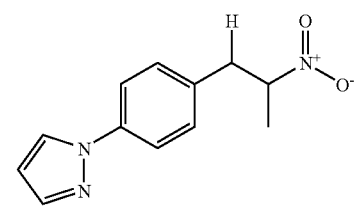

A mixture comprising 4-pyrazol-1-yl-benzaldehyde (7.0 g, 40.65 mmol), ammonium acetate (0.94 g, 12.19 mmol) and nitroethane (24 ml, 333.3 mmol) is stirred at reflux for 10 hours. The solvent is removed in vacuo and the resulting solid is dissolved in EtOAc and washed with water (3×50 ml). The organic portion is dried (MgSO$_4$) and concentrated in vacuo to afford the title compound as an orange solid. [MH+ 230.1].

Step 2: 1-(4-Pyrazol-1-yl-phenyl)-propan-2-one

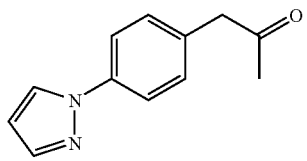

A stirred suspension comprising iron (10.7 g, 191.9 mmol) in glacial acetic acid (150 ml) under an inert atmosphere of argon is heated to 40° C. and then treated with a solution of 1-[4-(2-nitro-propyl)-phenyl]-1H-pyrazole (8.8 g, 38.39 mmol) in glacial acetic acid (100 ml). The reaction mixture is heated to 100° C. for 2 hours and then allowed to cool to room temperature. The mixture is poured onto ice-water (200 ml), stirred for 5 minutes and then filtered through celite washing through with DCM (50 ml). The organic portion of the filtrate is separated and the aqueous is extracted with DCM (150 ml). The organic portions are combined, washed with water (3×50 ml), brine (1×25 ml), dried (MgSO$_4$) and concentrated in vacuo to afford the title compound as a red oil. [MH+ 201.25].

Step 3: 4-Methyl-5-(4-pyrazol-1-yl-phenyl)-thiazol-2-ylamine

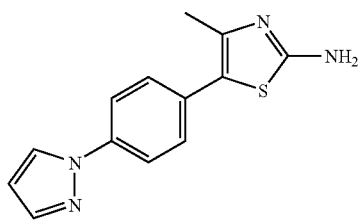

A solution of 1-(4-pyrazol-1-yl-phenyl)-propan-2-one (6.9 g, 34.46 mmol) in pyridine (30 ml) is treated with thiourea (2.6 g, 34.46 mmol) followed by iodine (8.7 g, 34.46 mmol) and heated to 80° C. After 8 hours, the reaction mixture is allowed to cool to room temperature and the resulting suspension is filtered and washed with EtOAc. The filtrate is concentrated in vacuo to afford an oil. The oil is dissolved in EtOAc (200 ml) and washed with NaHCO$_3$ (2×100 ml), brine (100 ml), dried (MgSO$_4$) and concentrated in vacuo to afford a sticky solid. EtOH is added to the crude residue and the resulting precipitate is filtered and dried to afford the title compound (MH+ 257.29).

Alternatively, 4-methyl-5-(4-pyrazol-1-yl-phenyl)-thiazol-2-ylamine may be prepared via the 'Suzuki' pathway:

Step 3a: Benzhydrylidene-[4-methyl-5-(4-pyrazol-1-yl-phenyl)-thiazol-2-yl]-amine

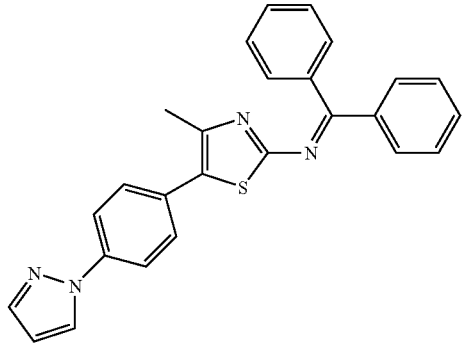

1-(4-Phenyl boronic acid)-1H-pyrazole (preparation described below) (275 mg, 1.44 mmol), benzhydrylidene-(5-bromo-4-methyl-thaizol-2-yl)-amine (Intermediate A1 step 2) (468 mg, 1.31 mmol), Pd$_2$(dba)$_3$ (12 mg, 0.013 mmol), and PCy$_3$ (87 mg, 0.31 mmol) are stirred under argon, in a solution of dioxane (4 ml) and aqueous potassium phosphate (1.76 ml, 2.23 mmol). The mixture is heated at 100° C. for 18 h. The excess solvent is removed in vacuo and the residue pre-absorbed onto silica. Purification by chromatography on silica eluting with gradient mixtures 10%-30% ethyl acetate in iso-hexane affords the title compound.

Preparation of 1-(4-phenyl boronic acid)-1H-pyrazole

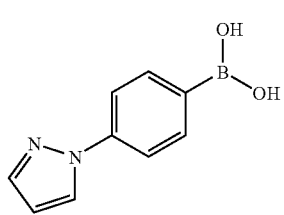

1-(4-Iodophenyl)-1H-pyrazole (7.71 g, 28.5 mmol) is dissolved in THF (100 ml), under inert conditions. Triethyl boronate (4.9 ml, 29.07 mmol) is added and the mixture cooled to −78° C. n-Butyl lithium is added slowly maintaining the temperature at −78° C. The mixture is allowed to warm to room temperature over 18 h. 5M Hydrochloric acid (30 ml) is added, the mixture stirred for 1 h and extracted with ethyl acetate (2×200 ml). The combined organics are washed with brine (250 ml), 10% sodium thiosulfate solution (250 ml) and 6M sodium hydroxide solution (250 ml). The product is precipitated from the basic solution on addition of 5M hydrochloric acid. The solid is filtered and dried in vacuo. [MH+ 189.06]

Step 3b: 4-Methyl-5-(4-pyrazol-1-yl-phenyl)-thiazol-2-ylamine

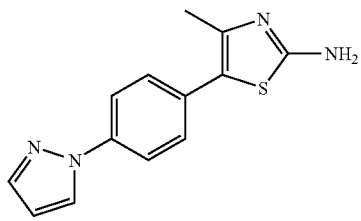

This compound is prepared from benzhydrylidene-[4-methyl-5-(4-pyrazol-1-yl-phenyl)-thiazol-2-yl]-amine analogously to 1-[4-(2-amino-4-methyl-thiazol-5-yl)-phenyl]-ethanone (Intermediate A1 step 4).

Step 4: Imidazole-1-carboxylic acid [4-methyl-5-(4-pyrazol-1-yl-phenyl)-thiazol-2-yl]-amide

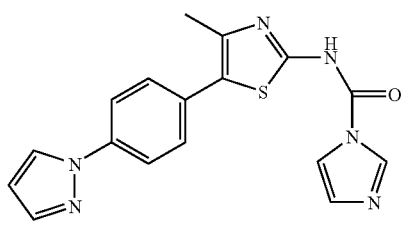

A suspension of 4-methyl-5-(4-pyrazol-1-yl-phenyl)-thiazol-2-ylamine (1.5 g, 5.85 mmol) in dry DCM is treated with CDI (1.1 g, 7.02 mmol) followed by TEA (1.2 ml, 8.77 mmol). The resulting orange suspension is heated to reflux for 3 hours and then allowed to cool to room temperature overnight. The suspension is filtered and washed with DCM to afford the title compound. [MH+ 315.35].

This solid consists of the imidazole-urea intermediate (A1) together with variable amounts of the corresponding isocyanate and imidazole which resulted from reversible thermal elimination of imidazole under the reaction conditions. This solid is used in the subsequent steps since the imidazole-urea intermediate and isocyanate intermediate are equally suitable as precursors to ureas.

Intermediate A3: Imidazole-1-carboxylic acid [5-(4-acetyl-3-fluoro-phenyl)-4-methyl-thiazol-2-yl]-amide

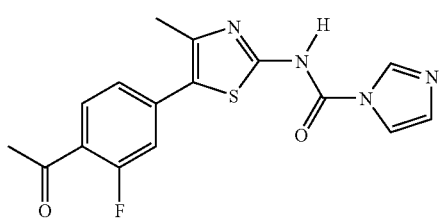

Step 1: N-(4-Methyl-thiazol-2-yl)-acetamide

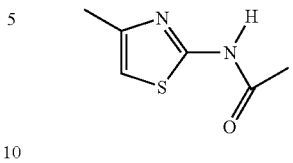

To a stirred, cooled (5° C.) solution of acetic anhydride (237 ml, 2.51 mol) is added portionwise 2-amino-4-methyl thiazole (80 g, 0.697 mol). To allow dissolution of the 2-amino-4-methyl thiazole, the reaction mixture is allowed to warm but kept below 35° C. Once a solution forms, the reaction mixture is cooled to 5° C. and stirred overnight. The solvent is removed in vacuo and the solid is dried in a vacuum oven overnight. The resulting solid is triturated with iso-hexane (100 ml) and dried again. Recrystallisation from EtOAc/iso-hexane affords the title product as a pale yellow solid.

The following syntheses are representative of the 'Heck' pathway to the compounds of formula (I) via intermediates of formula (VI):

Step 2: N-[5-(4-Acetyl-3-fluoro-phenyl)-4-methyl-thiazol-2-yl]-acetamide

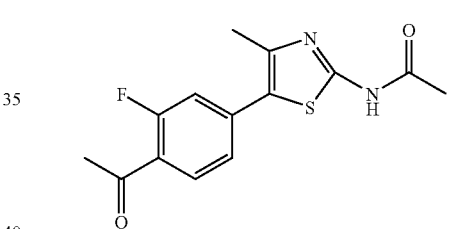

Dry, degassed DMF (25 ml) is added to 1-(4-bromo-2-fluoro-phenyl)-ethanone (WO 2003095441) (1.25 g, 5.76 mmol), N-(4-methyl-thiazol-2-yl)-acetamide (0.75 g, 4.80 mmol), Bis (tri-t-butylphosphine) palladium (0) (0.245 g, 0.48 mmol) and caesium carbonate (3.13 g, 9.60 mmol), and the reaction mixture heated to 150° C. for 4 hours. The reaction mixture is filtered through celite and the filtrate reduced in vacuo. Purification of the crude product by chromatography on silica eluting with 2:1 iso-hexane:EtOAc affords the title compound as a yellow solid. (MH+) 293.25

Step 3: 1-[4-(2-Amino-4-methyl-thiazol-5-yl)-2-fluoro-phenyl]-ethanone

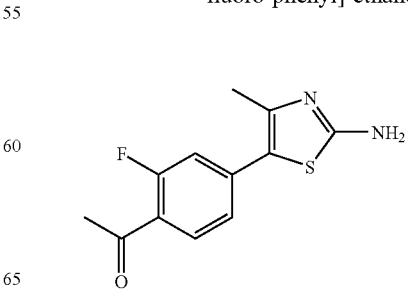

N-[5-(4-Acetyl-3-fluoro-phenyl)-4-methyl-thiazol-2-yl]-acetamide (0.46 g, 0.171 mmol) in EtOH (15 ml) is treated with 6M HCl (3.14 ml) and heated using microwave radiation at 100° C. After 90 minutes, the solvent is removed in vacuo and the resulting solid is dissolved in water (25 ml). The pH is adjusted to pH 7 by addition of 2M NaOH. The yellow solid which precipitates is filtered and dried under vacuum to afford the title compound. (MH+ 251.22).

Step 4: Imidazole-1-carboxylic acid [5-(4-acetyl-3-fluoro-phenyl)-4-methyl-thiazol-2-yl]-amide

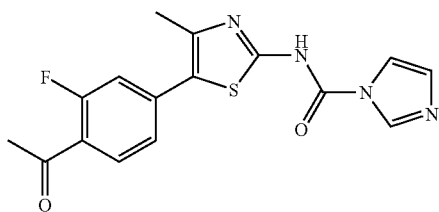

Dry DCM (10 ml) is added to 1-[4-(2-amino-4-methyl-thiazol-5-yl)-2-fluoro-phenyl]-ethanone (0.25 g, 1.0 mmol) and CDI (0.259 g, 1.6 mmol) and the mixture is heated at reflux for 4 hours. The resulting suspension is filtered and dried under vacuum to afford the title compound.

Intermediate A4: Imidazole-1-carboxylic acid [5-(4-methylsulfonyl-3-fluoro-phenyl)-4-methyl-thiazol-2-yl]-amide It may be prepared as disclosed in WO05/021519A2.

Intermediate A5: Imidazole-1-carboxylic acid [5-(4-pyridyl)-4-methyl-thiazol-2-yl]-amide It may be prepared as disclosed in WO04/096797A1.

Intermediate B1:
3-Amino-N-(5-methyl-isoxazol-3-yl)-propionamide hydroiodide

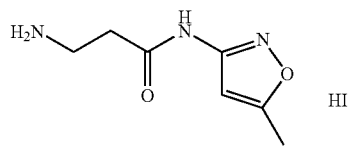

Step 1: [2-(5-Methyl-isoxazol-3-ylcarbamoyl)-ethyl]-carbamic acid tert-butyl ester

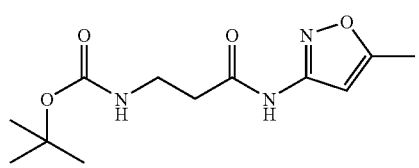

A solution of HOAT (0.216 g, 1.58 mmol) and WSCD (0.985 g, 6.34 mmol) in DCM (4 ml) is treated with 5-methyl-isoxazole-3-ylamine (0.57 g, 5.81 mmol) and N-Boc-β-ana-line (1.0 g, 5.28 mmol) and stirred at room temperature for 18 h. The resulting mixture is diluted with DCM (10 ml) and washed with water followed by brine. The organic portion is dried (MgSO$_4$) and concentrated in vacuo and the crude residue is purified by chromatography on silica eluting with EtOAc-EtOH (increasing polarity if necessary) to afford the title compound.

Step 2:
3-Amino-N-(5-methyl-isoxazol-3-yl)-propionamide hydroiodide

To a stirred solution of [2-(5-methyl-isoxazol-3-ylcarbamoyl)-ethyl]-carbamic acid tert-butyl ester (0.1 g, 0.37 mmol) in MeCN (3 ml) is added dropwise TMSI (0.11 ml, 0.74 mmol). After 30 minutes, MeOH (1 ml) is added to afford a yellow suspension which is collected by filtration and washed with EtOAc to afford the title compound. Further product is obtained by concentration of the filtrate.

Alternatively, this intermediate may be prepared as the hydrochloride salt:

A solution of DMAP (9.77 g), TEA (55.23 ml) and N,N'-diisopropylcarbodiimide (49.01 ml) in DCM is treated with 5-methyl-isoxazole-3-ylamine (28.8 g) and Boc-β-Ala-OH (50 g) and stirred at room temperature for 18 h. The resulting mixture is diluted with DCM (1750 ml) and washed with 10% citric acid (2×500 ml), saturated sodium hydrogen carbonate solution (2×500 ml), and brine (600 ml). The organic portion is dired (MgSO$_4$), concentrated in vacuo and the crude residue is stirred with iso-hexane (750 ml) for 1 hr. The resulting solid is dissolved in dioxane (400 ml) and treated with 4M HCl in dioxane (350 ml). After 1 hr the precipitate is filtered off and washed with dioxane (100 ml) to afford the 3-amino-N-(5-methyl-isoxazol-3-yl)-propionamide hydrochloride. (MH+ 169.84)

Intermediate B2:
3-Amino-N-pyridin-3-yl-propionamide hydroiodide

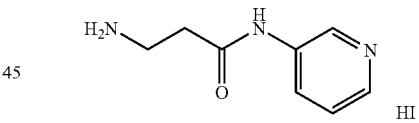

Step 1: [2-(Pyridin-3-ylcarbamoyl)-ethyl]-carbamic acid tert-butyl ester

TEA (2.2 ml, 16 mmol) is added to a stirred solution of BOC-β-alanine (2.4 g, 12.7 mmol), HOAt (0.68 g, 5.0 mmol), EDCl.HCl (2.43 g, 12.7 mmol) in DCM and stirred at room temperature. After 1 hour, 3-aminopyridine (1.0 g, 10.6 mmol) is added and the mixture is stirred at room temperature for a further 3 hours. The mixture is then diluted with DCM (200 ml) and washed with 0.1 M HCl followed by 1M NaOH. The organic portion is dried (MgSO$_4$) and concentrated in vacuo to afford the title compound as a white crystalline solid.

Step 2: 3-Amino-N-pyridin-3-yl-propionamide hydroiodide

To a stirred suspension of [2-(pyridin-3-ylcarbamoyl)-ethyl]-carbamic acid tert-butyl ester (0.075 g, 0.28 mmol) in MeCN (3 ml) is added dropwise TMSI (0.05 ml, 0.34 mmol).

After 30 minutes, MeOH (1 ml) is added and stirring continued for a further 20 minutes. The solvent is removed in vacuo and the crude residue is triturated with MeOH/EtOAc to afford the title compound as a cream crystalline solid.

Intermediates B3:
2-Amino-N-pyridin-3-yl-propionamide hydroiodide

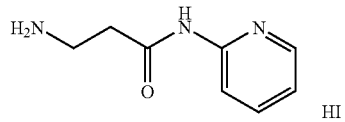

This compound is prepared analogously to Intermediate B2 by replacing 3-aminopyridine with 2-aminopyridine.

Intermediates B4:
3-Amino-N-isoxazol-3-yl-propionamide hydrochloride

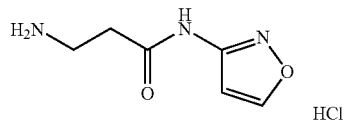

Step 1: [2-(Isoxazol-3-ylcarbamoyl)-ethyl]-carbamic acid tert-butyl ester

A mixture comprising BOC-β-alanine (1 g, 5.29 mmol), WSCD (0.985 g, 6.34 mmol) and HOAT (0.216 g, 1.59 mmol) in DCM is treated with 3-aminoisoxazole (0.43 ml, 5.81 mmol) and left stirring overnight. The resulting mixture is washed with water, brine, dried (MgSO$_4$) and concentrated in vacuo. The crude product is purified by chromatography on silica eluting with EtOAc to afford the title compound as a white solid.

Step 2: 3-Amino-N-isoxazol-3-yl-propionamide hydrochloride

[2-(Isoxazol-3-ylcarbamoyl)-ethyl]-carbamic acid tert-butyl ester (0.702 g, 2.76 mmol) in dioxane (5 ml) is treated with 4M HCl in dioxane (3.44 ml) and stirred at room temperature for 3 days. The solvent is removed in vacuo and co-evaporated with toluene to afford the title compound as a pale brown solid.

The deprotection process can also be carried out using TMSI as described in the preparation of Intermediate B2 (step 2).

Intermediate B5: 3-Amino-N-(2,5-dimethyl-2H-pyrazol-3-yl)-propionamide

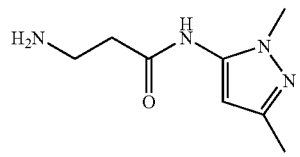

This compound is prepared analogously to Intermediate B4 by replacing 3-aminoisoxazole (step 1) with 1,3-dimethylpyrazole-5-amine.

Intermediate B6:
3-Amino-N-(2-naphthyl)-propionamide

This compound is commercially available.

EXAMPLE 1

3-{3-[4-Methyl-5-(4-pyrazol-1-yl-phenyl)-thiazol-2-yl]-ureido}-N-pyridin-3-yl-propionamide

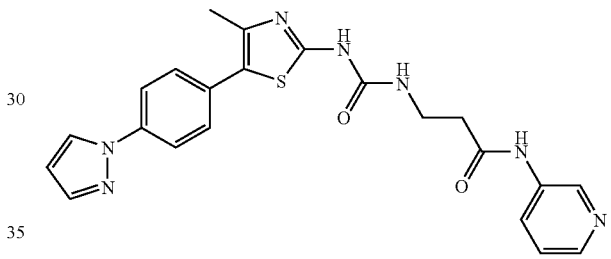

A stirred suspension of imidazole-1-carboxylic acid [4-methyl-5-(4-pyrazol-1-yl-phenyl)-thiazol-2-yl]-amide (Intermediate A1) (0.1 g, 0.28 mmol) and 3-amino-N-pyridin-3-yl-propionamide hydroiodide (Intermediate B2) (0.083 g, 0.28 mmol) in dry DMF (1 ml) is treated with TEA. After stirring at room temperature for 1 hour, the solvent is removed in vacuo and purification of the crude residue by chromatography on silica eluting with EtOAc/EtOH (10:1 increasing to 5:1) affords a solid which is recrystallised from EtOAc/EtOH to yield the title compound. [MH+ 448.49]

EXAMPLE 2

N-(5-Methyl-isoxazol-3-yl)-3-{3-[4-methyl-5-(4-pyrazol-1-yl-phenyl)-thiazol-2-yl]-ureido}-propionamide

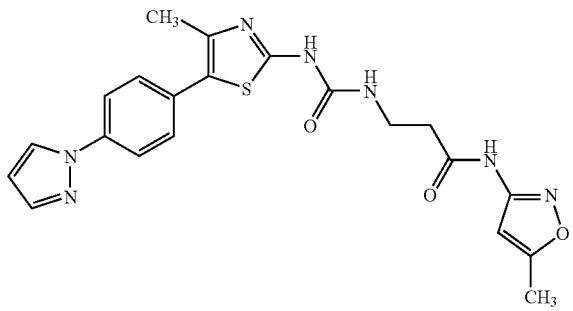

A mixture of 3-amino-N-(5-methyl-isoxazol-3-yl)-propionamide hydrochloride (Intermediate B1 produced by HCl deprotection) (0.1 g, 0.49 mmol) and triethylamine (0.164 ml, 1.18 mmol) is stirred in DMF (4 ml). Imidazole-1-carboxylic acid [4-methyl-5-(4-pyrazol-1-yl-phenyl)-thiazol-2-yl]-amide (Intermediate A2) (0.16 g, 0.47 mmol) is added and the mixture stirred at room temperature for 18 h. Water (20 ml) is added and the mixture stirred for 30 min. The solid is filtered off, washed with water and dried in vacuo at 45° C. for 4 h to afford the title compound.

By following the procedure as disclosed below, compounds of formula XI

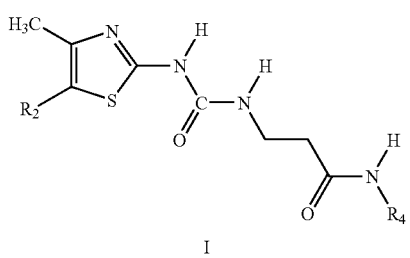

XI are shown in Table 1 below. The compounds are obtained in free form.

General Procedure for the Preparation of Further Examples from Midazole-urea Intermediates (A) and Amines (B)

The amine (B) (0.12 mmol) in dry DMF (0.12 mmol) is added to a solution/suspension of the imidazole urea intermediate (A) (0.12 mmol) in DMF (1.0 ml). Triethylamine may be added to enhance reaction rate and especially if one or both of the starting materials is present as a salt (1.1 equivalents $Et_3N$ per equiv. salt). The reaction mixture may be sonicated if necessary until a clear solution is obtained. The reaction is allowed to proceed at between room temperature and 70° C. until the starting material is consumed (30 minutes to 24 hours). When complete, the mixture is concentrated in vacuo to remove the solvent. The product may be purified by standard procedure, e.g. crystallisation, chromatography or HPLC.

TABLE 1

| Ex. | $R_2$ | $R_4$ | M/s MH+ |
|---|---|---|---|
| 3 | | | 448.50 |
| 4 | | | 482.17 |

TABLE 1-continued

| Ex. | $R_2$ | $R_4$ | M/s MH+ |
|---|---|---|---|
| 5 | | | 468.16 |
| 6 | | | 459.12 |
| 7 | | | 432.16 |
| 8 | | | 428.45 |
| 9 | | | 446.45 |

The compounds of formula I in free form or in pharmaceutically acceptable salt form, exhibit valuable pharmacological properties, e.g. as inhibitors of phosphatidylinositol 3-kinase enzymes (PI3K), particularly the δ isoform, e.g. as indicated in vitro and in vivo tests and are therefore indicated for therapy.

The compounds of formula I show inhibitory effect on PI3Kδ isoform as determined in following assays:

PI3K delta enzyme assay based on Scintillation Proximity Assay (SPA) technology. Human PI3K delta is expressed as a recombinant protein in insect cells. PI3K delta activity is assayed by measuring the phosphorylation of phosphatidylinositol (PI) using a scintillation proximity assay. Briefly, the kinase reaction is performed in a final volume of 50 μl/well. The final concentrations of ATP and PI in the assay are 5 μM and 6 μg/ml, respectively. The reaction is started by the addition of PI3K delta and terminated by the addition of 50 μl Wheatgerm agglutinin SPA beads after 90 minutes of incubation at room temperature. In this assay the compounds of formula I exhibit $IC_{50}$ values (concentrations required for 50% inhibition) ranging from 7 nM to 275 nM. For instance, the compound of Example 2 has an $IC_{50}$ value of 5 nM.

Compounds of formula I demonstrate selectivity over the α, β or γ isoforms as determined by a corresponding assay using the corresponding PI3K isoform. In particular, Compounds of formula I, e.g. Compound of Example 2, possess a selectivity for the δ isoform over the α, β or γ isoform of at least 10 fold, preferably at least 20 fold, more preferably at least 40 fold, as measured by the ratio of the $IC_{50}$ value of the compound for the δ isoform to the $IC_{50}$ value of the compound for the α, β or γ isoform.

Cellular PI3K delta assay. Rat-1 cells are transiently transfected with a human PI3K delta construct (pcDNA3 PIK3 delta containing a CaaX box at the C-terminal end) using the FUGENE transfection kit. The CaaX box signals for the attachment of an isoprenoid moiety which activates PI3K delta by targeting it to intracellular membranes/the plasma membrane. Subsequent, PI3K delta-dependent Akt phosphorylation is quantified in presence and absence of compounds to be tested using the phospho Akt ELISA kit from R&D Systems. Percent inhibition by the samples is calculated and the concentrations required for 50% inhibition ($IC_{50}$ values) are determined. In this assay the compounds of formula I have an $IC_{50}$ value $\leq 1$ µM; for instance, the compound of Example 2 has a $IC_{50}$ of 22 nM.

Furthermore, the compounds of formula I inhibit B and T cell responses in following assays:

B cell proliferation assay. A spleen cell suspension of nu/nu Balb/c mice is prepared and adjusted to $2 \times 10^6$ cells/ml in complete Iscoves Medium followed by the addition of 10 µg/ml monoclonal anti-mouse IgM antibody (clone b-7-6). Compounds to be rested are dissolved in DMSO at 10 mM and diluted in complete Iscoves Medium. 100 µl of the cell suspension are transferred to wells containing 100 µl compound solution resulting in end concentrations of $2 \times 10^5$ cells/well and 5 µg/ml monoclonal anti-mouse IgM antibody. Plates are incubated for 3 days at 37° C. and 5% $CO_2$. Cell proliferation is measured by incorporation of [$^3$H] thymidine following a 16 hours pulse. Percent inhibition by the compound to be tested is calculated and the concentrations required for 50% inhibition ($IC_{50}$ values) are determined. In this assay, the compounds of formula I exhibit an $IC_{50} < 1$ µM. For instance, the compound of example 2 has an $IC_{50}$ of 15 nM.

Mixed lymphocyte reaction (MLR). A two-way MLR is performed according to standard procedures. Briefly, spleen cells from CBA and BALB/c mice ($1.6 \times 10^5$ cells from each strain per well in flat bottom tissue culture microtiter plates, $3.2 \times 10^5$ in total) are incubated in RPMI medium containing 10% fetal calf serum, 100 U/ml penicillin, 100 µg/ml streptomycin, 50 µM 2-mercaptoethanol and serially diluted compounds to be tested. After four days of incubation 1 µCi [$^3$H] thymidine is added to the cultures. Cells are harvested after an additional five-hour incubation period, and incorporated $^3$H-thymidine is determined according to standard procedures. Percent inhibition by the samples is calculated and the concentrations required for 50% inhibition ($IC_{50}$ values) are determined. In this assay, the compounds of formula I have ICsovalues ranging from 20 nM to 200 nM. Compound of Example 2, for instance has an $IC_{50}$ value of 26 nM.

The compounds of formula I show effectiveness in inhibiting inflammatory conditions, for example in inflammatory airways diseases, as demonstrated in an animal model, e.g. a mouse or rat model, of airways inflammation or other inflammatory conditions, for example as described by Szarka et al, *J. Immunol. Methods* (1997) 202:49-57; Renzi et al, *Am. Rev. Respir. Dis.* (1993) 148:932-939; Tsuyuki et al., *J. Clin. Invest.* (1995) 96:2924-2931; and Cernadas et al (1999) *Am. J. Respir. Cell Mol. Biol.* 20:1-8.

The compounds of formula I in free or pharmaceutically acceptable salt form are, therefore, useful in the treatment and/or prevention of conditions, diseases or disorders which are mediated by the activation of the Pi3 kinase enzymes, particularly inflammatory, allergic or autoimmune conditions.

Accordingly, compounds of formula I are useful in the treatment of inflammatory or obstructive airways diseases, resulting, for example, in reduction of tissue damage, airways inflammation, bronchial hyper-reactivity, remodelling or disease progression. Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma; occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g. of acute asthmatic or bronchoconstrictor attack, improvement in lung function or improved airways hyper-reactivity. It may further be evidenced by reduced requirement for other, symptomatic therapy, i.e. therapy for or intended to restrict or abort symptomatic attack when it occurs, for example anti-inflammatory (e.g. corticosteroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g. between the hours of about 4 to 6 am, i.e. at a time normally substantially distant form any previously administered symptomatic asthma therapy.

Other inflammatory or obstructive airways diseases and conditions to which the present invention is applicable include acute lung injury (ALI), adult respiratory distress syndrome (ARDS), chronic obstructive pulmonary, airways or lung disease (COPD, COAD or COLD), including chronic bronchitis or dyspnea associated therewith, emphysema, as well as exacerbation of airways hyper-reactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, cystic fibrosis, ptilosis, siderosis, silicosis, tabacosis and byssinosis.

Having regard to their anti-inflammatory activity, in particular in relation to inhibition of eosinophil activation, agents of the invention are also useful in the treatment of eosinophil related disorders, e.g. eosinophilia, in particular eosinophil related disorders of the airways (e.g. involving morbid eosinophilic infiltration of pulmonary tissues) including hyper-eosinophilia as it effects the airways and/or lungs as well as, for example, eosinophil-related disorders of the airways consequential or concomitant to Löffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

The compounds of formula I are furthermore indicated in the treatment of inflammatory or allergic conditions of the skin, for example psoriasis, irritant contact dermatitis, allergic contact dermatitis, and further eczematous dermatitises, seborrhoeic dermatitis, cutaneous manifestations of immunologically-mediated disorders, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, and other inflammatory or allergic conditions of the skin.

The compounds of formula I are also indicated for the prevention or treatment of other diseases or conditions, in particular diseases or conditions having an inflammatory component, for example treatment of diseases and conditions of the eye such as conjunctivitis, keratoconjunctivitis sicca and vernal conjunctivitis, and inflammatory disease in which autoimmune reactions are implicated or having an autoimmune component or aetiology, including autoimmune haematological disorders, e.g. haemolytic anemia, aplastic anemia, pure red cell anemia, idiopathic thrombocytopenia and pernicious anemia, systemic lupus erythematosus, polychondritis, scleroderma, Wegener granulomatosis, dermatomyositis, hashimoto's thyroidis, myasthenia gravis, Steven-Johnson syndrome, idiopathic sprue, autoimmune inflammatory diseases optionally with underlying aberrant reactions, e.g. inflammatory bowel disease, Crohn's disease or ulcerative colitis, endocrine opthalmopathy, Grave's disease, sarcoidosis, alveolitis, chronic hypersensitivity pneumonitis, multiple sclerosis, primary billiary cirrhosis, uveitis, interstitial lung fibrosis, psoriatic arthritis and inflammatory glomerular injury, e.g. glomerulonephritis (with and without nephrotic syndrome, e.g. including idiopathic nephrotic syndrome or minal change nephropathy).

Other diseases or conditions which may be treated with agents of the invention include acute or chronic rejection of cell, tissue or organ allo- or xenografts or delayed graft function, graft versus host disease, thrombosis, hypertension, heart ischemia, pancreatitis, septic shock, rheumatoid arthritis, osteoarthritis, psoriatic arthritis, proliferative diseases such as cancer, atherosclerosis, obesity, restenosis, diabetes type I or II and the disorders associated therewith, vasculitis, Sjoegren syndrome, Graves opthalmopathy, retinopathy, such as diabetic retinopathy or hyperbaric oxygen-induced retinopathy, conditions characterized by elevated intraocular pressure or secretion of ocular aqueous humor, such as glaucoma, and others, allergic diseases, e.g. allergic rhinitis/conjunctivitis, diarrhoeal diseases, inflammatory lung injury, inflammatory liver injury, cystitis, e.g. interstitial cystitis or urinary incontinence including bladder detrusor hyper-reflexia and bladder hypersensitivity, inflammatory eye disease, keratoconjunctivitis, myocarditis or hepatitis, e.g. acute or chronic hepatitis, ischemia/reperfusion injury, e.g. myocardial infarction, stroke, heart failure such as (acute and chronic) congestive heart failure, left ventricular dysfunction including impaired cardiac contractility, hypertrophic cardiomyopathy, diabetic cardiac myopathy and other types of detrimental cardiac dysfunction and remodeling, gut ischemia, renal failure or hemorrhage shock, traumatic shock, nephrotic syndrome, infectious diseases, e.g. toxic shock (e.g. superantigen induced), adult respiratory distress syndrome or viral infections, e.g. AIDS, viral hepatitis, e.g. hepatitis B or C, chronic bacterial infection, or neurodegenerative diseases, e.g. Alzheimer disease, amyotrophic lateral sclerosis or senile dementia. Examples of cell, tissue or solid organ transplants include e.g. pancreatic islets, stem cells, bone marrow, corneal tissue, neuronal tissue, heart, lung, combined heart-lung, kidney, liver, bowel, pancreas, trachea or oesophagus. For the above uses the required dosage will of course vary depending on the mode of administration, the particular condition to be treated and the effect desired.

In general, satisfactory results are indicated to be obtained systemically at daily dosages of from about 0.03 to 10.0 mg/kg per body weight. An indicated daily dosage in the larger mammal, e.g. humans, is in the range from about 0.5 mg to about 1 g, conveniently administered, for example, in divided doses up to four times a day or in retard form. Suitable unit dosage forms for oral administration comprise from ca. 0.1 to 500 mg active ingredient.

The compounds of formula I may be administered by any conventional route, in particular enterally, e.g. orally, e.g. in the form of tablets or capsules, or parenterally, e.g. in the form of injectable solutions or suspensions, topically, e.g. in the form of lotions, gels, ointments or creams, by inhalation, for example in the treatment of inflammatory or obstructive airways disease, intranasally, for example in the treatment of allergic rhinitis, or in a suppository form. Pharmaceutical compositions comprising a compound of formula I in free form or in pharmaceutically acceptable salt form in association with at least one pharmaceutical acceptable carrier or diluent may be manufactured in conventional manner by mixing with a pharmaceutically acceptable carrier or diluent.

The compounds of formula I may be administered in free form or in pharmaceutically acceptable salt form e.g. as indicated above. Such salts may be prepared in conventional manner and exhibit the same order of activity as the free compounds.

In accordance with the foregoing the present invention further provides:

1.1 A method for preventing or treating conditions, disorders or diseases mediated by the activation of the Pi3 kinase enzymes, e.g. the δ isoform, e.g. such as indicated above, in a subject in need of such treatment, which method comprises administering to said subject an effective amount of a compound of formula I or a pharmaceutically acceptable salt thereof;

1.2 A method for preventing or treating acute or chronic transplant rejection or allergic or inflammatory or autoimmune diseases, e.g. as indicated above, in a subject in need of such treatment, which method comprises administering to said subject an effective amount of a compound of formula I or a pharmaceutically acceptable salt thereof;

2. A compound of formula I, in free form or in a pharmaceutically acceptable salt form for use as a pharmaceutical, e.g. in any of the methods as indicated under 1.1 or 1.2 above.

3. A pharmaceutical composition, e.g. for use in any of the methods as in 1.1 or 1.2 above comprising a compound of formula I in free form or pharmaceutically acceptable salt form in association with a pharmaceutically acceptable diluent or carrier therefore.

4. A compound of formula I or a pharmaceutically acceptable salt thereof for use in the preparation of a pharmaceutical composition for use in any of the method as in 1.1 or 1.2 above.

The compounds of formula I or a pharmaceutically acceptable salt thereof may be administered as the sole active ingredient or in conjunction with, e.g. as an adjuvant to, other drugs e.g. immunosuppressive or immunomodulating agents or other anti-inflammatory agents, e.g. for the treatment or prevention of allo- or xenograft acute or chronic rejection or inflammatory or autoimmune disorders, or a chemotherapeutic agent, e.g a malignant cell anti-proliferative agent. For example, the compounds of formula I may be used in combination with a calcineurin inhibitor, e.g. cyclosporin A or FK 506; a mTOR inhibitor, e.g. rapamycin, 40-O-(2-hydroxyethyl)-rapamycin, CCI779, ABT578, AP23573, biolimus-7 or biolimus-9; an ascomycin having immuno-suppressive properties, e.g. ABT-281, ASM981, etc.; corticosteroids;

cyclophosphamide; azathioprene; methotrexate; leflunomide; mizoribine; mycophenolic acid or salt; mycophenolate mofetil; 15-deoxyspergualine or an immunosuppressive homologue, analogue or derivative thereof; a PKC inhibitor, e.g. as disclosed in WO 02/38561 or WO 03/82859, e.g. the compound of Example 56 or 70; a SIP receptor agonist or modulator, e.g. FTY720 optionally phosphorylated or an analog thereof, e.g. 2-amino-2-[4-(3-benzyloxyphenylthio)-2-chlorophenyl]ethyl-1,3-propanediol optionally phosphorylated or 1-{4-[1-(4-cyclohexyl-3-trifluoromethyl-benzyloxyimino)-ethyl]-2-ethyl-benzyl}-azetidine-3-carboxylic acid or its pharmaceutically acceptable salts; a JAK3 kinase inhibitor, e.g. N-benzyl-3,4-dihydroxy-benzylidene-cyanoacetamide α-cyano-(3,4-dihydroxy)-]N-benzylcinnamamide (Tyrphostin AG 490), prodigiosin 25-C (PNU156804), [4-(4'-hydroxyphenyl)-amino-6,7-dimethoxyquinazoline] (WHI-P131), [4-(3'-bromo-4'-hydroxylphenyl)-amino-6,7-dimethoxyquinazoline] (WHI-P154), [4-(3',5'-dibromo-4'-hydroxylphenyl)-amino-6,7-dimethoxyquinazoline] WHI-P97, KRX-211, 3-{(3R,4R)-4-methyl-3-[methyl-(7H-pyrrolo[2,3-d]pyrimidin-4-yl)-amino]-piperidin-1-yl}-3-oxo-propionitrile, in free form or in a pharmaceutically acceptable salt form, e.g. mono-citrate (also called CP-690,550), or a compound as disclosed in WO 04/052359 or WO 05/066156; immunosuppressive monoclonal antibodies, e.g., monoclonal antibodies to leukocyte receptors, e.g., MHC, CD2, CD3, CD4, CD7, CD8, CD25, CD28, CD40, CD45, CD52, CD58, CD80, CD86 or their ligands; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y; adhesion molecule inhibitors, e.g. LFA-1 antagonists, ICAM-1 or -3 antagonists, VCAM-4 antagonists or VLA-4 antagonists; or a chemotherapeutic agent, e.g. paclitaxel, gemcitabine, cisplatinum, doxorubicin or 5-fluorouracil; or an anti-infectious agent.

The compounds of formula I or a pharmaceutically acceptable salt thereof are also useful as co-therapeutic agents for use in combination with other drug substances such as anti-inflammatory, bronchodilatory, antihistamine or antitussive drug substances, particularly in the treatment of obstructive or inflammatory airways diseases such as those mentioned hereinbefore, for example as potentiators of therapeutic activity of such drugs or as a means of reducing required dosaging or potential side effects of such drugs.

Suitable anti-inflammatory drugs include steroids, in particular glucocorticosteroids such as budesonide, beclamethasone dipropionate, fluticasone propionate, ciclesonide or mometasone furoate, or steroids described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/035668, WO 03/048181, WO 03/062259, WO 03/064445, WO 03/072592, non-steroidal glucocorticoid receptor agonists such as those described in WO 00/00531, WO 02/10143, WO 03/082280, WO 03/082787, WO 03/104195, WO 04/005229; LTB4 antagonists such LY293111, CGS025019C, CP-195543, SC-53228, BIIL 284, ONO 4057, SB 209247 and those described in U.S. Pat. No. 5,451,700; LTD4 antagonists such as montelukast and zafirlukast; PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID (TM) CC-10004 (Celgene), VM554/UM565 (Vernalis), T-440 (Tanabe), KW-4490 (Kyowa Hakko Kogyo), and those disclosed in WO 92/19594, WO 93/19749, WO 93/19750, WO 93/19751, WO 98/18796, WO 99/16766, WO 01/13953, WO 03/104204, WO 03/104205, WO 03/39544, WO 04/000814, WO 04/000839, WO 04/005258, WO 04/018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607 and WO 04/037805; Ata agonists such as those disclosed in EP 409595A2, EP 1052264, EP 1241176, WO 94/17090, WO 96/02543, WO 96/02553, WO 98/28319, WO 99/24449, WO 99/24450, WO 99/24451, WO 99/38877, WO 99/41267, WO 99/67263, WO 99/67264, WO 99/67265, WO 99/67266, WO 00/23457, WO 00/77018, WO 00/78774, WO 01/23399, WO 01/27130, WO 01/27131, WO 01/60835, WO 01/94368, WO 02/00676, WO 02/22630, WO 02/96462, WO 03/086408, WO 04/039762, WO 04/039766, WO 04/045618 and WO 04/046083; A2b antagonists such as those described in WO 02/42298; and beta-2 adrenoceptor agonists such as albuterol (salbutamol), metaproterenol, terbutaline, salmeterol fenoterol, procaterol, and especially, formoterol and pharmaceutically acceptable salts thereof, and compounds (in free or salt or solvate form) of formula I of WO 0075114, which document is incorporated herein by reference, preferably compounds of the Examples thereof, especially the compound 5-[(R)-2-(5,6-Diethyl-indan-2-ylamino)-1-hydroxy-ethyl]-8-hydroxy-1H-quinolin-2-one, and pharmaceutically acceptable salts thereof, as well as compounds (in free or salt or solvate form) of formula I of WO 04/16601, and also compounds of WO 04/033412.

Suitable bronchodilatory drugs include anticholinergic or antimuscarinic agents, in particular ipratropium bromide, oxitropium bromide, tiotropium salts and CHF 4226 (Chiesi), and glycopyrrolate, but also those described in WO 01/04118, WO 02/51841, WO 02/53564, WO 03/00840, WO 03/87094, WO 04/05285, WO 02/00652, WO 03/53966, EP 424021, U.S. Pat. Nos. 5,171,744, 3,714,357, WO 03/33495 and WO 04/018422.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine as well as those disclosed in WO 03/099807, WO 04/026841 and JP 2004107299.

Other useful combinations of agents of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, Takeda antagonists such as N-[[4-[[[6,7-dihydro-2-(4-methylphenyl)-5H-benzocyclohepten-8-yl]carbonyl]amino]phenyl]-methyl]tetrahydro-N,N-dimethyl-2H-pyran-4-aminium chloride (TAK-770), and CCR-5 antagonists described in U.S. Pat. No. 6,166,037 (particularly claims 18 and 19), WO 00/66558 (particularly claim 8), WO 00/66559 (particularly claim 9), WO 04/018425 and WO 04/026873.

Compounds of formula I may also be combined with an angiotensin receptor blocker, e.g. valsartan (an angiotensin receptor blocker), losartan, irbesartan, eprosartan, forasartan, olmesartan, ripisartan, saprisartan, candesartan, tasosartan or telmisartan.

Compounds of formula I may also be used in combination with a chemotherapeutic agent, e.g. paclitaxel, gemcitabine, cisplatinum, doxorubicin, 5-fluorouracil, a hormonal agent or antagonist, e.g. an anti-androgen or mitoxantrone, an antiestrogen, e.g. tamoxifen, fulvestrant, raloxifene and raloxifene hydrochloride, an aromatase inhibitor, e.g. atamestane, exemestane and formestane and, in particular, non-steroids, especially aminoglutethimide, roglethimide, pyridoglutethimide, trilostane, testolactone, ketokonazole, vorozole, fadrozole, anastrozole or letrozole, an antimetabolite, a plant alkaloid, a biological response modifier, preferably a lymphokine or interferons, an inhibitor of protein tyrosine kinase and/or serine/threonine kinase, or an agent with other or unknown mechanism of action, e.g. any epitholone or epitholone derivative.

Where the compounds of formula I are administered in conjunction with another drug, e.g. as disclosed above, dosages of the co-administered drug will of course vary depending on the type of co-drug employed, on the specific drug employed, on the condition being treated and so forth. In accordance with the foregoing the present invention provides in a yet further aspect:

5. A method as defined above comprising co-administration, e.g. concomitantly or in sequence, of a therapeutically effective non-toxic amount of a compound of formula I or a pharmaceutically acceptable salt thereof, and at least a second drug substance, e.g. as indicated above.

6. A pharmaceutical combination, e.g. a kit, comprising a) a first agent which is a compound of formula I as disclosed herein, in free form or in pharmaceutically acceptable salt form, and b) at least one co-agent, e.g. as disclosed above. The kit may comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of formula I and a co-agent, are both administered to a patient simultaneously in the form of a single entity or dosage. The term "non-fixed combination" means that the active ingredients, e.g. a compound of formula I and a co-agent, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more active ingredients.

The invention claimed is:

1. A compound of formula I

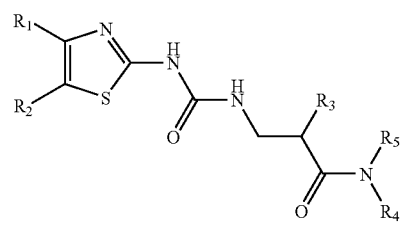

I wherein
$R_1$ is $C_{1-3}$alkyl;
$R_2$ is phenyl, naphthyl or biphenylyl, each being optionally substituted by one or more substituents selected from halogen, $SO_2C_{1-3}$alkyl, acyl and a 5 or 6 membered heteroaryl; or an optionally substituted 5- or 6- membered heteroaryl;
$R_3$ is H or $C_{1-3}$alkyl;
$R_4$ is phenyl, naphthyl or biphenylyl, each being optionally substituted by $C_{1-4}$alkyl; or an optionally substituted 5- or 6- membered heteroaryl comprising at least one N as heteroatom; provided that $R_4$ is other than naphthyl when $R_2$ is phenyl substituted by and optionally halogen; and
$R_5$ is H or $C_{1-3}$alkyl;
or a salt thereof.

2. A compound according to claim 1, wherein $R_1$ is methyl.

3. A compound according to claim 1, wherein $R_3$ is H.

4. A compound according to claim 1, wherein $R_5$ is H.

5. A compound according to claim 1, wherein $R_2$ is phenyl substituted by halogen, $SO_2C_{1-3}$alkyl, $C(O)C_{1-3}$alkyl or a 5 membered heteroaryl; or a 5 or 6 membered heteroaryl.

6. A compound according to claim 1, wherein $R_4$ is naphthyl or a 5 or 6 membered heteroaryl optionally substituted by $C_{1-3}$alkyl.

7. A pharmaceutical composition comprising a compound according to claim 1 and a pharmaceutically acceptable excipient.

* * * * *